United States Patent [19]

Thurber et al.

[11] 4,353,829

[45] Oct. 12, 1982

[54] PROCESS FOR 5-AROYLATION OF 1,2-DIHYDRO-3H-PYRROLO[1,2-A]PYRROLE-1-CARBOXYLIC ESTERS

[75] Inventors: T. C. Thurber, Los Altos; Derek Tegg, Palo Alto, both of Calif.

[73] Assignee: Syntex (U.S.A.) Inc., Palo Alto, Calif.

[21] Appl. No.: 208,920

[22] Filed: Nov. 21, 1980

[51] Int. Cl.³ ............................................ C07D 487/04
[52] U.S. Cl. ............................................... 260/326.25
[58] Field of Search ..................... 260/326.25, 326.31

[56] References Cited

U.S. PATENT DOCUMENTS 4,087,539 5/1978 Muchowski et al. ............... 424/274
4,089,969 5/1978 Muchowski et al. .......... 260/326.46
4,097,579 6/1978 Muchowski et al. ............... 424/274
4,232,038 11/1980 Kluge et al. ..................... 260/326.46

OTHER PUBLICATIONS

White et al.; J. Org. Chem., vol. 42, No. 26, pp. 4248–4252, (1977).

*Primary Examiner*—Mary C. Lee
*Attorney, Agent, or Firm*—Tom M. Moran; Alan M. Krubiner

[57] ABSTRACT

An improved process for 5-aroylation of 1,2-dihydro-3H-pyrrolo[1,2-a]pyrrole-1-carboxylic esters and nitriles and for subsequent hydrolysis thereof is disclosed. In the improved process, an aroyl morpholide is reacted with the pyrrolo pyrrole system and the resultant decomposed with base.

25 Claims, No Drawings

PROCESS FOR 5-AROYLATION OF 1,2-DIHYDRO-3H-PYRROLO[1,2-A]PYRROLE-1-CARBOXYLIC ESTERS

BACKGROUND OF THE INVENTION

1. Field of the Invention

The present invention relates to a process for 5-aroylation of 1,2-dihydro-3H-pyrrolo[1,2-a]pyrrole-1-carboxylic esters or nitriles. The aroylated esters or nitriles are then optionally converted to the corresponding acids which are useful as antiinflammatory agents.

2. Prior Art

U.S. Pat. Nos. 4,087,539, 4,097,579, and 4,140,698, and U.S. applications Ser. Nos. 71,443, now U.S. Pat. No. 4,232,038, 71,444, now abandoned, and 157,719; disclose a method for 5-aroylation of 1,2-dihydro-3H-pyrrolo[1,2-a]pyrrole-1-carboxylic esters of nitriles to form first the corresponding 5-aroyl ester or nitrile, and then subsequent hydrolysis of that ester or nitrile to form the correponding free carboxylic acids. In the method therein described, the aroyl moiety is supplied in the form of the dimethylamide, and the reaction is carried out in the presence of an inorganic acid halide and an inert solvent. The resulting intermediate complex is then hydrolyzed by base to the 5-aroyl-1,2-dihydro-3H-pyrrolo[1,2-a]pyrrole-1-carboxylic ester or nitrile; then stronger base or more vigorous conditions, followed by acidification, converts the ester or nitrile to acid. These previously disclosed processes have been unsatisfactory due to low yields and poor scalabilty.

Other methods of aroylation of the pyrrole nucleus, when not a part of the pyrrolopyrrole bicyclo system include reaction with an aroyl halide (U.S. Pat. No. 3,998,844) and with a 2-aryldithiolanium cation (U.S. Pat. No. 4,119,639). However, these methods suffer from the disadvantages of non-specificity as to the position aroylated and/or undue complexity and cost of reagent. In a manner more analogous to the previously described aroylation of pyrrolopyrroles using the aroyl dimethylamide, isolated pyrrole nuclei can be reasonably specifically aroylated using the corresponding aroyl morpholides, according to the description of White, J. and McGillivray, G.; J. Org. Chem. 42: 4248 (1977). Although these authors found that the morpholides were, in general, better reagents than the corresponding dimethylamides, they also found that alkyl (methyl) substitution at the ring nitrogen decreases the rate of reaction by a factor of 100 relative to the unsubstituted pyrrole when the morpholide is used. They attribute this decrease to steric factors related to the transition state. It is therefore implied that use of the morpholide would be disadvantageous for N-substituted pyrroles.

It is, therefore, quite surprising that substitution of the morpholide for the dimethylamide in the aroylation of the pyrrolopyrrole (which is, of course, substituted at the N-position of the pyrrole ring) enhances the rate of aroylation by a factor of approximately ten over the dimethylamide. The increase in rate is significant for reasons other than mere convenience because yields are enhanced in this process when reaction time is reduced. In addition, the morpholide reagent is intrinsically easier to handle than the dimethylamide.

SUMMARY OF THE INVENTION

Broadly, one aspect of the present invention relates to an improved process for preparation of the compounds of the formula

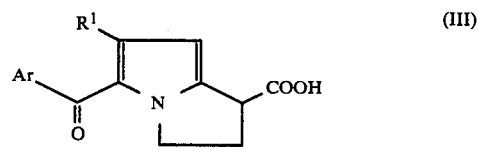

wherein
$R^1$ is hydrogen or lower alkyl; and
Ar is optionally substituted phenyl, or is selected from the group consisting of

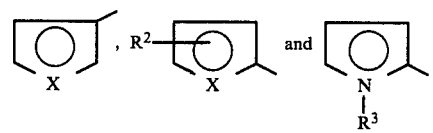

wherein X is O or S, $R^2$ is hydrogen, methyl, chloro or bromo, and can be at any position of the ring, and $R^3$ is hydrogen or lower alkyl; which compounds are useful as antiinflammatory agents; and of the compounds of the formula

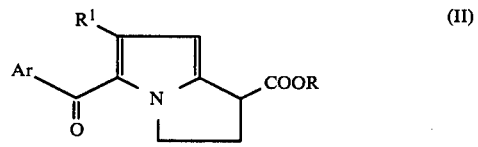

wherein
R is lower alkyl and $R^1$ and Ar are as herein defined. The improved process consists of a common first step: treating a compound of the formula

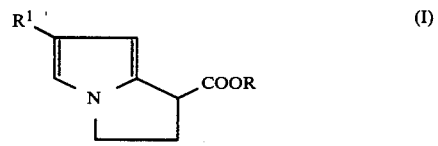

wherein R and $R^1$ are as herein defined, with a previously prepared mixture of an inorganic acid chloride and a compound of the formula:

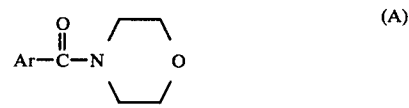

wherein Ar is as herein defined, in the presence of an inert aprotic solvent. This step is then followed by treatment with base.

If the subsequent treatment with base is carried out using only a weak base, a compound of formula II is produced. If the subsequent treatment with base is carried out either with a strong base alone, in a single step, or with a weak base followed by a strong base, in a two-step procedure, a compound of formula III is produced.

Another aspect of the present invention relates to a process for preparing a compound of formula II which comprises treating the resultant of reaction of A, inorganic acid chloride, and I, with weak base.

Another aspect relates to a process for preparing a compound of formula III which comprises treating the resultant of reaction of A, inorganic acid chloride, and I, with a strong base.

Still another aspect relates to preparing a compound of formula III by treating the resultant of reaction of A, inorganic acid chloride, and I, sequentially with a weak base and then a strong base.

In another aspect of the invention, the starting material is a nitrile of the formula:

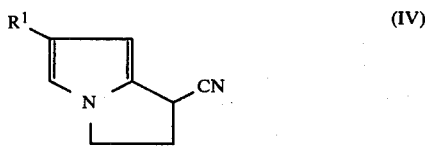

wherein $R^1$ is as defined previously, and the improved process comprises treating said nitrile with a previously prepared mixture of an inorganic acid chloride and a compound of formula A in the presence of an inert aprotic solvent, followed by treatment with weak or strong base to result in a product of the formula

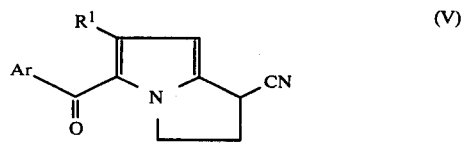

wherein Ar and $R^1$ are as previously defined.

DETAILED DESCRIPTION

Definitions

As used herein:

"Lower alkyl" means a saturated branched or unbranched hydrocarbon chain containing 1-6 carbons, such as for example, ethyl, n-hexyl, or t-butyl.

"Lower alkoxy" means —OR wherein R is lower alkyl as herein defined.

"Halogen" means fluoro, chloro, bromo or iodo.

"Weak base" means a substance, which, when dissolved in water at 1F concentration generates a pH between 7 and 9. Examples of such weak bases are sodium acetate, sodium bicarbonate, ammonia, primary amines and the like.

"Strong base" means a substance which, when dissolved in water at 1F concentration, generates a pH of greater than 10. Examples of such strong bases are sodium hydroxide, potassium hydroxide, sodium carbonate and the like.

"Optionally substituted" phenyl means substitution in ortho, meta or para positions by one to three substituents selected from the group consisting of halogen, lower alkyl or lower alkoxy.

"Polar solvent" means either water, or methanol, ethanol or propanol, or aqueous mixture of these alcohols.

Typical Process

The reactions which comprise the three alternative processes of the present invention as it relates to the starting material of formula I are shown in the Reaction Scheme I below:

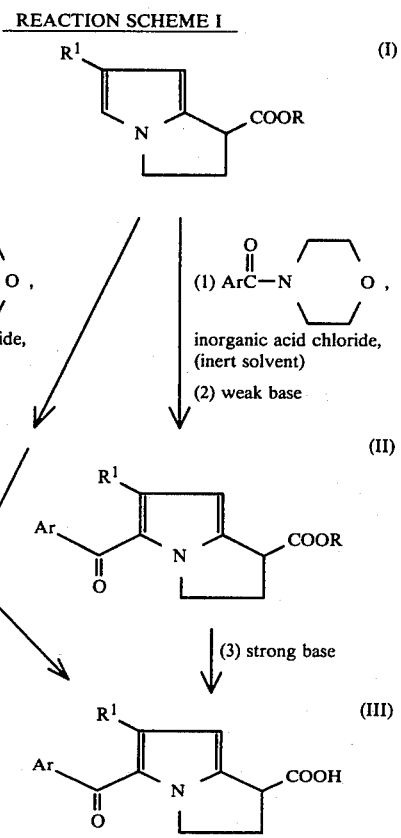

The compound of formula I is in all cases treated first with the aroyl morpholide in the presence of an inorganic acid halide. The aroyl morpholide is prepared essentially by the method of White (supra) in which the appropriate aroyl halide is reacted with an approximately equimolar amount of morpholine in the presence of triethylamine.

The resulting aroyl morpholide is mixed with an inorganic acid halide, such as $POCl_3$, $POBr_3$, $SO_2Cl_2$ and the like; preferably $POCl_3$. The relative amounts are not critical. Optionally an inert organic solvent such as ethane dichloride, chloroform, or carbon tetrachloride, but preferably methylene dichloride, may be included in this mixture. The presence of the solvent, however, is not particularly advantageous in all cases. The mixture is agitated, preferably stirred, for about 0.5–36 hours, preferably 1–5 hours at about 30°–50°; preferably 40°–45°.

A solution of the pyrrolopyrrole substrate of formula I in an inert solvent, most preferably $CH_2Cl_2$, is then added to the above mixture. Again the ratio of reactants is not critical, but it is preferable that the molar amount of the substrate be slightly less than the molar amount of the minority reactant in the prepared morpholide/halide mixture. The resulting reaction mixture is kept at about 30°–70°, preferably 40°–45° until the desired reaction has taken place; usually about 1–8 hours, most usually 1.5–3 hours.

The entire procedure to this point is carried out in an inert atmosphere in order to exclude water. Any anhydrous gas could be used, but nitrogen is the most convenient choice. As the reaction is scaled up, the problem of water in the ambient air becomes smaller because of less proportional available surface area. However, it has been found prudent to use nitrogen as a matter of routine.

The intermediate formed at this point cannot conveniently be isolated, but must be hydrolyzed either to the ester of formula II, or to the free acid of formula III.

If it is desired to prepare a compound of formula III, a single step procedure is preferred. In this embodiment, the reaction mixture is poured into a solution in polar solvent, preferably aqueous, of a strong base, such as a mineral hydroxide or carbonate, preferably sodium hydroxide. A large excess of the base is used. The mixture is then kept at about 30°–100°, preferably 40°–60° until reaction is complete.

Alternatively, if the two-step procedure is to be used, or a compound of formula II is to be prepared, an amount of from about 3 to about 10 molar equivalents of sodium acetate or other weak base may be added directly to the reaction mixture, followed by an additional reaction time of about 4–6 hours during which the mixture is refluxed. At the end of this period, the compound of formula II is produced.

If subsequent conversion to the compound of formula III is desired, further hydrolysis is carried out in a conventional manner with an alkali metal hydroxide or carbonate in an aqueous or aqueous lower aliphatic alcohol (methanol, ethanol, etc.) solution. The temperature is about room temperature to reflux and the reaction time about 15 minutes to about 3 hours. Preferably, the hydrolysis is effected with aqueous methanolic potassium carbonate at reflux temperatures for about 30 minutes.

The compounds of formula II or III may be isolated by conventional means, such as extraction into volatile solvents, precipitation and filtration, crystallization, chromatography and the like; or combinations of such procedures. For compounds of formula III, the isolation is best carried out by neutralizing with acid, e.g. with HCl, and then extracting the neutralized free acid form of the compound into a volatile solvent, e.g. $CH_2Cl_2$, with subsequent conventional treatment to isolate pure product.

The reaction which comprises the process of the invention as it relates to the starting material of formula IV is shown in Reaction Scheme II:

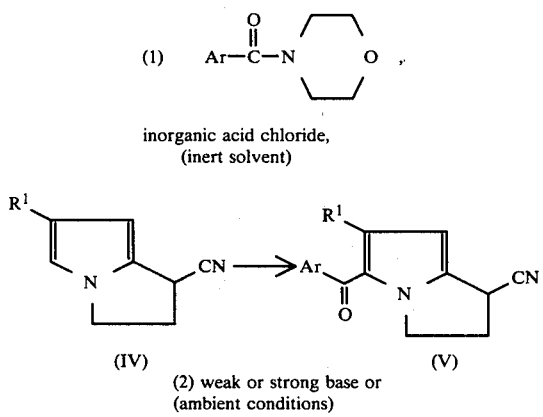

Treatment with the aroyl morpholide and inorganic acid chloride is carried out as outlined hereinabove. The subsequent treatment with base is effected by mixing this reaction mixture with a solution of either weak or strong base dissolved in a polar solvent such as water, ethanol, methanol and the like, preferably water. Preferred bases are sodium acetate or sodium carbonate. The reaction is carried out without heating, at ambient temperature, and proceeds rapidly to completion, within about 1–10 minutes.

The resulting compound of formula IV may be hydrolyzed to a compound of formula III by treatment with acid or base under more vigorous conditions. Procedures for this conversion are described in U.S. Pat. No. 4,140,698 which is incorporated herein by reference.

Preferred Embodiments

In a preferred embodiment of the invention, $POCl_3$ and an aroyl morpholide in approximately equimolar ratio is used as the aroylating mixture. A preferred reaction temperature range is 40°–45°.

The solvent of choice for the pyrrolopyrrole substrate is methylene chloride.

Preferred aroyl morpholides are those wherein Ar in the formula

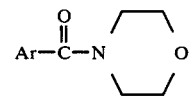

is optionally substituted phenyl.

In a preferred embodiment of the hydrolysis procedure, to give a compound of formula III, the reaction mixture containing inorganic acid halide, morpholide and substrate is added to an aqueous sodium hydroxide solution of 1–10 M.

Preferred compounds of formula I and IV for use in the invention are those wherein $R^1$ is methyl or hydrogen, and (for formula I) R is methyl.

The following examples are intended to illustrate the invention, but are not to be construed as limiting its scope.

EXAMPLE 1

Benzoylation of methyl 1,2-dihydro-3H-pyrrolo[1,2-a]pyrrole-1-carboxylate with hydrolysis to the free acid.

A. Benzmorpholide (1.45 gm, 7.90 mmole), was placed in a 25 ml round bottom flask. $POCl_3$ (1.25 ml, 13.4 mmole) was added. This was stirred and heated in a 40° oil bath for 2.5 hours.

A solution of methyl 1,2-dihydro-3H-pyrrolo[1,2-a]-pyrrole-1-carboxylic ester (1.00 gm, 6.10 mmole) in 3.4 ml $CH_2Cl_2$ was added and heating was continued for 2 hours, at this time, thin layer chromatography (TLC) of the reaction mixture showed reaction to be complete.

The reaction mixture was added carefully to a solution of NaOH (3.09 gm, 77.3 mmole) in 10 ml $H_2O$, allowing the $CH_2Cl_2$ to boil off, and the mixture heated to 50°. More NaOH (1.30 gm, 32.5 mmole) was added. TLC 15 minutes later showed complete hydrolysis. The mixture was cooled and extracted with 2×10 ml $CH_2Cl_2$. The aqueous layer was acidified by the addition of 3.30 ml (39.6 mmole) conc. HCl. A milk formed. This was extracted with 5×10 ml $CH_2Cl_2$. Extract numbers 1–4 were dried ($Na_2SO_4$) and charcoaled (Darco 660), then evaporated to a tan solid, which was a mixture of all benzoyl isomers. This solid was dissolved in 10 ml 2-propanol and hexane (10 ml) was added. A crystalline solid formed slowly.

The first crop had a weight of 0.90 gm (58.5%) and was pure (by TLC) 5-benzoyl-1,2-dihydro-3H-pyrrolo-[1,2-a]pyrrole-1-carboxylic acid. A second crop (0.35 g, 23%), which was contaminated by other isomers, formed on evaporation the supernatant to 2 ml of 2-propanol and adding 2 ml hexane.

B. In a manner similar to that in Part A, and substituting for benzmorpholide
 p-methoxybenzmorpholide,
 2,4-dichlorobenzmorpholide,
 3-methylbenzmorpholide,
 2-furanoylmorpholide,
 2-thenoylmorpholide,
 3-thenoylmorpholide,
 3-ethyl-2-thenoylmorpholide,
 4-n-butyl-2-furanoylmorpholide,
 2-pyrroylmorpholide, or
 1-methylpyrroylmorpholide, one obtains
 5-(p-methoxybenzoyl)-1,2-dihydro-3H-pyrrolo[1,2-a]-pyrrole-1-carboxylic acid,
 5-(2,4-dichlorobenzoyl)-1,2-dihydro-3H-pyrrolo[1,2-a]pyrrole-1-carboxylic acid,
 5-(3-methylbenzoyl)-1,2-dihydro-3H-pyrrolo[1,2-a]-pyrrole-1-carboxylic acid,
 5-(2-furanoyl)-1,2-dihydro-3H-pyrrolo[1,2-a]-pyrrole-1-carboxylic acid.
 5-(2-thenoyl)-1,2-dihydro-3H-pyrrolo[1,2-a]-pyrrole-1-carboxylic acid,
 5-(3-thenoyl)-1,2-dihydro-3H-pyrrolo[1,2-a]-pyrrole-1-carboxylic acid,
 5-(3-ethyl-2-thenoyl)-1,2-dihydro-3H-pyrrolo[1,2-a]-pyrrole-1-carboxylic acid,
 5-(4-n-butyl-2-furanoyl)-1,2-dihydro-3H-pyrrolo[1,2-a]pyrrole-1-carboxylic acid,
 5-(2-pyrroyl)-1,2-dihydro-3H-pyrrolo[1,2-a]pyrrole-1-carboxylic acid, or
 5-(1-methylpyrroyl)-1,2-dihydro-3H-pyrrolo[1,2-a]pyrrole-1-carboxylic acid.

EXAMPLE 2

Benzoylation of methyl 1,2-dihydro-3H-pyrrolo[1,2-a]pyrrole-1-carboxylate

Benzmorpholide, (15.23 gm. 79.67 mmole) was dissolved in 15.3 ml $CH_2Cl_2$. $POCl_3$ (6.87 ml, 76 mmole) was added. This was heated in a 42° oil bath overnight. A solution of the methyl 1,2-dihydro-3H-pyrrolo[1,2-a]-pyrrole-1-carboxylic ester, 10.0 gm, 61 mmole) in 15 ml $CH_2Cl_2$ was added. Heating was continued at 42° bath for 1.5 hours.

The reaction was shown to be complete by TLC. The resulting light brown solution was transferred with a 10 ml $CH_2Cl_2$ wash to a separatory funnel. The funnel was placed on a 500 ml 3 neck flask, which was also equipped with a reflux condenser and mechanical stirrer. $H_2O$ (67 ml) and NaOH (24.9 gm, 0.62 mole) were placed in the flask. The reaction mixture was added dropwise to the NaOH solution over 45 minutes with stirring and allowing the $CH_2Cl_2$ to reflux in the condenser. After the addition was complete the mixture was stirred at ambient temperature for 30 minutes. The hydrolysis was shown to be complete by TLC.

In the isolation procedure for the product, 6 N HCl (40 ml) was added. The lower organic layer was removed, and pH of upper aqueous phase was shown to be 8-9 (paper). The aqueous layer was then extracted with 2×30 ml $CH_2Cl_2$, which removed a small amount of product. The aqueous layer was then acidified to pH 2-3 (paper) by the addition of 18 ml 6 N HCl. A milk was formed, which was extracted with $CH_2Cl_2$ (1×60 ml, 2×20 ml), to extract the majority of the product.

The extracts from the acidified aqueous $CH_2Cl_2$ were combined, washed with 2×30 ml $H_2O$, dried ($Na_2SO_4$) and evaporated to a solid (11.4 gm). This was dissolved in 50 ml $CH_2Cl_2$ and hexane (50 ml) was added, and a solid crystallized overnight.

The above extracts from the neutral (pH 8-9) mixture were combined and extracted with 2×25 ml 1 N NaOH. The NaOH solutions were then combined, washed with 25 ml $CH_2Cl_2$ and acidified with 9 ml 6H HCl. A milk formed, which was extracted with 2×25 ml $CH_2Cl_2$. The $CH_2Cl_2$ was dried ($Na_2SO_4$) and evaporated to a solid (3.1 gm). The solid was then dissolved in 15 ml $CH_2Cl_2$, 15 ml hexane was added, and the mixture allowed to crystallize overnight. Both crystal crops were shown to be pure 5-benzoyl-1,2-dihydro-3H-pyrrolo[1,2-a]pyrrole-1-carboxylic acid by TLC.

| | | |
|---|---|---|
| wt. from acid $CH_2Cl_2$'s = 7.80 gm | (50.5%) | |
| wt. from neutral $CH_2Cl_2$'s = 2.30 gm | (14.9%) | |
| | 65.4% | total yield. |

EXAMPLE 3

Aroylation of 1,2-dihydro-3H-pyrrole[1,2-a]pyrrole-1-nitrile

Benzmorpholide (5.67 kg, 29.7 mole) was mixed with stirring with $POCl_3$ (4.88 l, 52.4 moles) under an atmosphere of nitrogen. The mixture was heated to 40°-43° for 6 hours.

The mixture was washed into a larger vessel with 1 liter methylene chloride, and mixed with a solution of 1,2-dihydro-3H-pyrrole[1,2-a]pyrrole-1-nitrile (3.238 kg, 24.5 moles) in 17.2 l of methylene chloride, all under nitrogen. The reaction mixture was brought to 42° and agitated under nitrogen overnight.

The mixture was then added to a solution of $Na_2CO_3$ (18.5 kg) in 60 l water. The temperature was kept at 40° C. for one-half hour, and then the mixture was cooled to 21° C.

Addition of both water and methylene chloride resulted in layer separation: When an initial total of 60 l water failed to result in separation, 80 l of the mixture was removed and treated with 20 l water and 20 l $CH_2Cl_2$. The layers were separated, the aqueous layer washed twice with 10 l portions of $CH_2Cl_2$. The remaining mixture (after the removal of the 80 l above) was treated with 40 l water and 20 l $CH_2Cl_2$; the layers separated, the aqueous layer was washed with the previously used $CH_2Cl_2$ washes. All organic fractions were then combined.

The solvent was removed by distillation and the resulting product cleaned up by adsorption of impurities onto silica gel. The silica gel was eluted for product with methylene chloride, which was then removed by distillation during replacement by methanol.

The product, 5-benzoyl-1,2-dihydro-3H-pyrrole[1,2-a]-pyrrole-1-nitrile crystallized from methanol to give 3.47 kg or 60% yield.

What is claimed is:

1. A process for preparing a compound of the formula

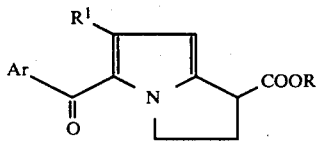

wherein
R is lower alkyl;
R¹ is hydrogen or lower alkyl; and
Ar is phenyl, optionally substituted by 1 to 3 substituents selected from the group consisting of halogen, lower alkyl, or lower alkoxy or is selected from the group consisting of

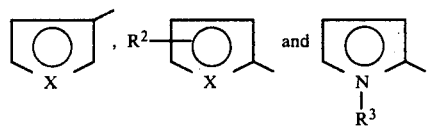

wherein X is O or S, R² is hydrogen, methyl, chloro or bromo; and R³ is hydrogen or lower alkyl;
which process comprises:
(a) treating a compound of the formula

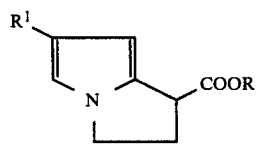

wherein
R and R¹ are as herein defined, with a mixture of an inorganic acid chloride and a compound of the formula:

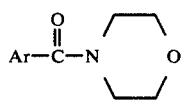

wherein Ar is as herein defined, optionally in the presence of an inert aprotic solvent, followed by
(b) mixing therewith a weak base.

2. The process of claim 1 wherein the inorganic acid chloride is POCl₃.

3. The process of claim 2 wherein the molar ratio of POCl₃ and compound of formula A is 1:1.

4. The process of claim 1 wherein Ar is an optionally substituted phenyl.

5. The process of claim 1 wherein R¹ is hydrogen or methyl and R is methyl.

6. A process for preparing a compound of the formula

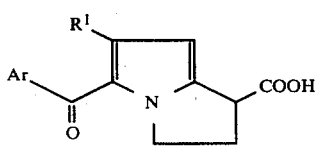

wherein

R¹ is hydrogen or lower alkyl; and
Ar is phenyl, optionally substituted by 1 to 3 substituents selected from the group consisting of halogen, lower alkyl, and lower alkoxy or is selected from the group consisting of

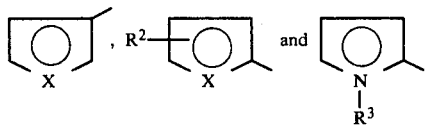

wherein X is O or S, R² is hydrogen, methyl, chloro or bromo; and R³ is hydrogen or lower alkyl; which process comprises
(a) treating a compound of the formula

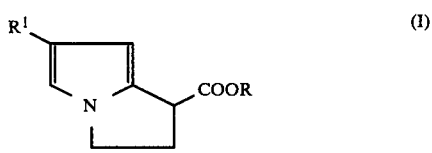

wherein
R is lower alkyl and R¹ is as herein defined with a mixture of an inorganic acid chloride and a compound of the formula:

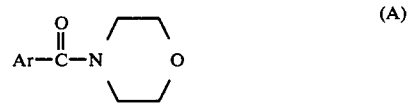

wherein Ar is as herein defined, optionally in the presence of an inert aprotic solvent, followed by
(b) mixing therewith water and a strong base.

7. The process of claim 6 wherein the inorganic acid chloride is POCl₃.

8. The process of claim 7 wherein the molar ratio of POCl₃ and compound of formula A is 1:1.

9. The process of claim 6 wherein Ar is optionally substituted phenyl.

10. The process of claim 6 wherein the strong base is sodium hydroxide.

11. The process of claim 6 wherein R¹ is hydrogen or methyl, and R is methyl.

12. A process for preparing a compound of the formula

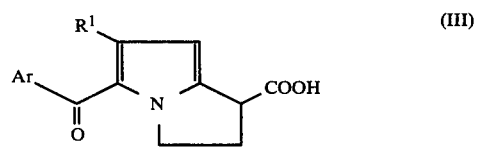

wherein
R¹ is hydrogen or lower alkyl; and
Ar is phenyl, optionally substituted by 1 to 3 substituents selected from the group consisting of halogen, lower alkyl, and lower alkoxy or is selected from the group consisting of

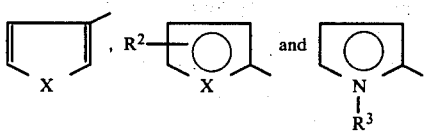

wherein X is O or S, $R^2$ is hydrogen, methyl, chloro or bromo; and $R^3$ is hydrogen or lower alkyl; which process comprises
(a) treating a compound of the formula:

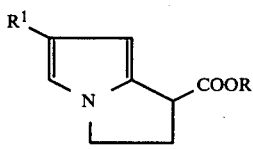

(II)

wherein
R is lower alkyl and $R^1$ is as herein defined, with a mixture of an inorganic acid chloride and a compound of the formula:

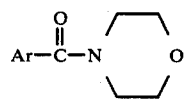

(A)

wherein Ar is as herein defined, optionally in the presence of an inert aprotic solvent, followed by
(b) mixing therewith water and a weak base to form a compound of the formula

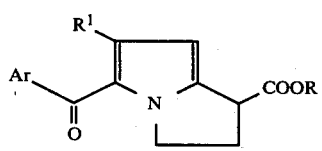

(II)

wherein
R, $R^1$ and Ar are as herein defined, followed by
(c) mixing with the compound of formula II a solution of strong base in a polar solvent.

13. The process of claim 12 wherein the inorganic acid chloride is $POCl_3$.

14. The process of claim 13 wherein the molar ratio of $POCl_3$ and compound of formula A is 1:1.

15. The process of claim 12 wherein Ar is optionally substituted phenyl.

16. The process of claim 12 wherein the strong base is sodium hydroxide.

17. The process of claim 12 wherein $R^1$ is hydrogen or methyl, and R is methyl.

18. A process for preparing a compound of the formula

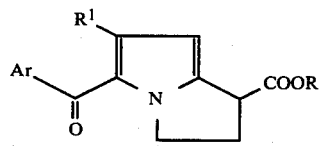

(II)

wherein
R is lower alkyl;

$R^1$ is hydrogen or lower alkyl; and
Ar is phenyl, optionally substituted by 1 to 3 substituents selected from the group consisting of halogen, lower alkyl, and lower alkoxy or is selected from the group consisting of

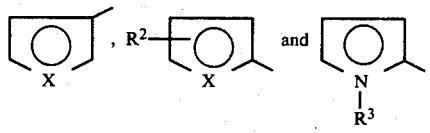

wherein X is O or S, $R^2$ is hydrogen, methyl, chloro or bromo; and $R^3$ is hydrogen or lower alkyl;
which process comprises:
treating the resultant of the reaction of a compound of the formula

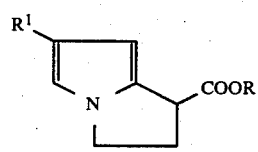

(I)

wherein $R^1$ and R are as herein defined, with an inorganic acid chloride and a compound of the formula

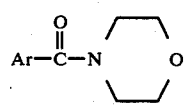

(A)

wherein Ar is a defined, with a weak base.

19. The process of claim 18 wherein Ar is optionally substituted phenyl.

20. The process of claim 18 wherein $R^1$ is hydrogen or methyl and R is methyl.

21. A process for preparing a compound of the formula

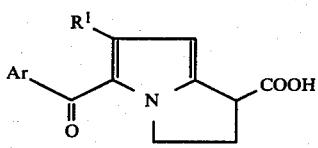

(III)

wherein
$R^1$ is hydrogen or lower alkyl; and
Ar is phenyl, optionally substituted by 1 to 3 substituents selected from the group consisting of halogen, lower alkyl, and lower alkoxy or is selected from the group consisting of

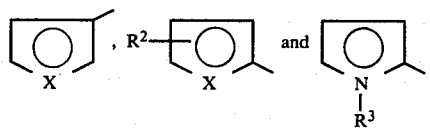

wherein X is O or S, $R^2$ is hydrogen, methyl, chloro or bromo; and $R^3$ is hydrogen or lower alkyl; which process comprises treating the resultant of the reaction of a compound of the formula

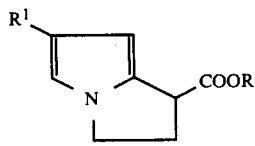
(I)

wherein R¹ is as herein defined and R is lower alkyl, with inorganic acid chloride and a compound of the formula

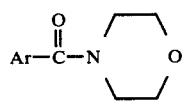
(A)

wherein Ar is a defined, with either
(1) water and a strong base, or
(2) water and a weak base, followed by treating with a solution of strong base in a polar solvent.

22. The process of claim 21 wherein Ar is optionally substituted phenyl.

23. The process of claim 21 wherein R¹ is hydrogen or methyl and R is methyl.

24. A process for preparing a compound of the formula

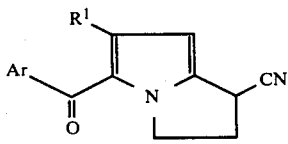
(V)

wherein
R¹ is hydrogen or lower alkyl; and
Ar is phenyl, optionally substituted by 1 to 3 substituents selected from the group consisting of halogen, lower alkyl, and lower alkoxy or is selected from the group consisting of

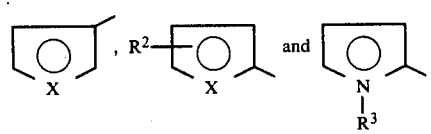

wherein X is O or S, R² is hydrogen, methyl, chloro or bromo; and R³ is hydrogen or lower alkyl;
which process comprises:
(a) treating a compound of the formula

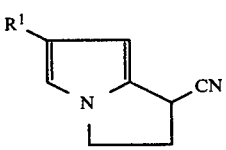
(IV)

wherein
R¹ is as herein defined with a mixture of an inorganic acid chloride and a compound of the formula

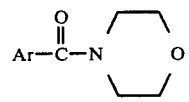
(A)

wherein Ar is as herein defined, optionally in the presence of an inert aprotic solvent, followed by
(b) mixing therewith a solution of base in polar solvent.

25. A process for preparing a compound of the formula

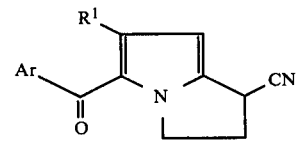
(V)

wherein
R¹ is hydrogen or lower alkyl; and
Ar is phenyl, optionally substituted by 1 to 3 substituents selected from the group consisting of halogen, lower alkyl, or lower alkoxy or is selected from the group consisting of

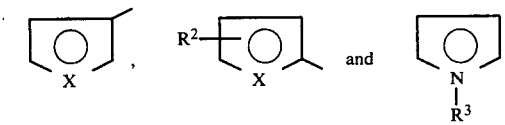

wherein X is O or S, R² is hydrogen, methyl, chloro or bromo; and R³ is hydrogen or lower alkyl; which process comprises treating the resultant of the reaction of a compound of the formula

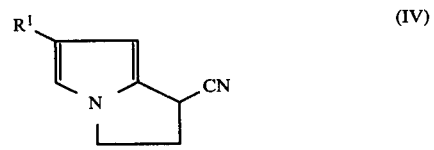
(IV)

wherein R¹ is as herein defined with inorganic acid chloride and a compound of the formula

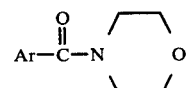
(A)

wherein Ar is as herein defined, with a solution of base in a polar solvent.

* * * * *